United States Patent
Arinobe et al.

(10) Patent No.: US 11,724,025 B2
(45) Date of Patent: Aug. 15, 2023

(54) ADMINISTERING INSTRUMENT AND DRUG SOLUTION ADMINISTERING SYSTEM

(71) Applicant: TERUMO KABUSHIKI KAISHA, Tokyo (JP)

(72) Inventors: Manabu Arinobe, Kanagawa (JP); Yusuke Hyakkan, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 118 days.

(21) Appl. No.: 17/038,610

(22) Filed: Sep. 30, 2020

(65) Prior Publication Data
US 2021/0008276 A1 Jan. 14, 2021

Related U.S. Application Data

(63) Continuation of application No. PCT/JP2019/013307, filed on Mar. 27, 2019.

(30) Foreign Application Priority Data

Mar. 30, 2018 (JP) .................. 2018-067418

(51) Int. Cl.
*A61M 5/142* (2006.01)
*A61M 5/14* (2006.01)
(Continued)

(52) U.S. Cl.
CPC ........ *A61M 5/14248* (2013.01); *A61M 5/145* (2013.01); *A61M 5/1413* (2013.01);
(Continued)

(58) Field of Classification Search
CPC .......... A61M 5/14244; A61M 5/14248; A61M 5/145; A61M 5/162
See application file for complete search history.

(56) References Cited

U.S. PATENT DOCUMENTS

2007/0135774 A1\* 6/2007 Turner .............. A61M 39/0247
604/288
2008/0294094 A1\* 11/2008 Mhatre .............. A61M 5/14248
604/65
(Continued)

FOREIGN PATENT DOCUMENTS

JP 2009233388 A 10/2009
WO 2007/056309 A2 5/2007

OTHER PUBLICATIONS

The extended European Search Report dated Apr. 14, 2021, by the European Patent Office in corresponding European Patent Application No. 19776375.8-1122. (6 pages).
(Continued)

*Primary Examiner* — Bhisma Mehta
*Assistant Examiner* — John J Crawford
(74) *Attorney, Agent, or Firm* — Buchanan Ingersoll & Rooney PC

(57) ABSTRACT

An administering instrument is disclosed, which is capable of preventing a needle tube from coming out of a living body during administration of a drug solution and a drug solution administering system including the administering instrument and a medicinal solution administering device. The administering instrument includes a puncture part that has a contact surface contacting a body surface H of a user, a needle holding part for holding a needle tube, and a communication passage communicating with a lumen of the needle tube. The puncture part includes a fixing part that is disposed above the contact surface and fixes the first end part of the tube to the puncture part in a state where the first end part of the tube is inclined toward the contact surface of the puncture part.

19 Claims, 4 Drawing Sheets

(51) Int. Cl.
    *A61M 5/145*     (2006.01)
    *A61M 5/162*     (2006.01)
    *A61M 39/12*     (2006.01)
(52) U.S. Cl.
    CPC .............. *A61M 5/162* (2013.01); *A61M 39/12* (2013.01); *A61M 2005/14252* (2013.01)

(56) References Cited

U.S. PATENT DOCUMENTS

| | | |
|---|---|---|
| 2013/0345633 A1 | 12/2013 | Chong |
| 2015/0105724 A1* | 4/2015 | Montalvo ......... A61M 5/16831 604/118 |
| 2015/0209508 A1 | 7/2015 | Constantineau et al. |
| 2017/0266369 A1 | 9/2017 | Cawthon et al. |

OTHER PUBLICATIONS

International Search Report (PCT/ISA/210) dated Jun. 25, 2019, by the Japan Patent Office as the International Searching Authority for International Application No. PCT/JP2019/013307.

Written Opinion (PCT/ISA/237) dated Jun. 25, 2019, by the Japan Patent Office as the International Searching Authority for International Application No. PCT/JP2019/013307.

* cited by examiner

ADMINISTERING INSTRUMENT AND DRUG SOLUTION ADMINISTERING SYSTEM

CROSS-REFERENCES TO RELATED APPLICATIONS

This application is a continuation of International Application No. PCT/JP2019/013307 filed Mar. 27, 2019, which claims priority to Japanese Application No. 2018-067418 filed on Mar. 30, 2018, the entire content of both of which is incorporated herein by reference.

FIELD OF THE INVENTION

The present disclosure generally relates to an administering instrument and a drug solution administering system including the administering instrument and a drug solution administering device.

BACKGROUND DISCUSSION

Syringe pump-type drug solution administering devices are known which administer a drug solution filled in a drug solution container to a living body by a pressing action of a plunger. Further, in administering a drug solution with a drug solution administering device of this type, an administering instrument is sometimes used which includes a puncture part (cannula housing) connected to the drug solution administering device via a predetermined connector and tube.

The puncture part provided in the administering instrument has a contact surface (bottom surface) that comes into contact with a body surface of a user. Further, the puncture part holds a needle tube arranged so as to project from the contact surface. The needle tube held by the puncture part supplies a drug solution fed from the drug solution container via a tube or the like to the living body with the needle tube puncturing the living body.

In the drug solution administering system, the administering instrument is attached to the body surface of the user via the contact surface of the puncture part while the drug solution is administered to the living body. Similarly, the drug solution administering device is attached to the body surface of the user through the contact surface (bottom surface) of the housing in which each member of the drug solution administering device is assembled. Therefore, while the drug solution is administered to the user, the puncture part of the administering instrument and the drug solution administering device are attached to the body surface of the user with the puncture part and the drug solution administering device connected to each other via the tube. For example, when the user moves such as twisting his/her body, the puncture part is pulled toward the drug solution administering device via the tube. Thereby, a force that lifts the puncture part from the body surface acts on the puncture part, which sometimes causes the puncture part to come off the body surface. Further, this possibly causes the needle tube held by the puncture part to come out of the living body.

For example, in a case where the drug solution administering device and the puncture part are attached to a curved body surface (for example, the abdomen, thigh, and so on) or where a thin puncture part is attached to the body surface and then a deviation (difference) in the height direction occurs between a position of the contact surface of the puncture part and a position of the contact surface of the drug solution administering device, a force that lifts the puncture part from the body surface via the tube is likely to act on the puncture part, which increases the possibility that the needle tube is removed from the living body.

SUMMARY

An administering instrument is disclosed that is capable of preventing a needle tube from coming out of a living body during administration of a drug solution, and to provide a drug solution administering system including the administering instrument and a drug solution administering device.

An administering instrument according to an aspect of the present disclosure is an administering instrument connectable to a drug solution administering device including a drug solution container in which a drug solution is filled. The administering instrument includes a connector that includes a communication part configured to communicate with a lumen of the drug solution container and is connectable to the drug solution administering device; a needle tube configured to puncture a living body; a puncture part including a contact surface that is provided in a lower end and configured to contact a body surface of the living body, a needle holding part that is provided above the contact surface to hold the needle tube so that a tip of the needle tube projects from the contact surface, and a communication passage communicating with a lumen of the needle tube; and a tube that includes a first end part connected to the puncture part, a second end part connected to the connector, and a tube body communicating from the first end part to the second end part and is configured to supply the drug solution from the lumen of the drug solution container to the needle tube via the communication part of the connector and the communication passage of the puncture part. The puncture part is disposed above the contact surface and includes a fixing part that fixes the first end part of the tube to the puncture part in a state where the first end part of the tube is inclined toward the contact surface of the puncture part.

According to another aspect, a drug solution administering system is disclosed, which includes an administering instrument connectable to a drug solution administering device, the drug solution administering device including a drug solution container in which a drug solution is filled. The administering instrument comprising: a connector that includes a communication part configured to communicate with a lumen of the drug solution container and is connectable to the drug solution administering device; a needle tube configured to puncture a living body; a puncture part including a contact surface that is provided in a lower end and configured to contact a body surface of the living body, a needle holding part that is provided above the contact surface to hold the needle tube so that a tip of the needle tube projects from the contact surface, and a communication passage communicating with a lumen of the needle tube; a tube that includes a first end part connected to the puncture part, a second end part connected to the connector, and a tube body communicating from the first end part to the second end part and is configured to supply the drug solution from the lumen of the drug solution container to the needle tube via the communication part of the connector and the communication passage of the puncture part; and wherein the puncture part is disposed above the contact surface and includes a fixing part that fixes the first end part of the tube to the puncture part in a state where the first end part of the tube is inclined toward the contact surface of the puncture part. The system also includes a housing that holds the drug solution container, and a plunger configured to push out the drug solution in the drug solution container to the tube.

According to an aspect of the present disclosure is an administering instrument connectable to a drug solution administering device including a drug solution container in which a drug solution is filled. The administering instrument includes a connector that includes a communication part capable of communicating with a lumen of the drug solution container and is connectable to the drug solution administering device; a needle tube configured to puncture a living body; a puncture part including a contact surface that is provided in a lower end to and configured to contact a body surface of the living body, a needle holding part that is provided above the contact surface to hold the needle tube so that a tip of the needle tube projects from the contact surface, and a communication passage communicating with a lumen of the needle tube; and a tube that includes a first end part connected to the puncture part, a second end part connected to the connector, and a tube body communicating from the first end part to the second end part and is configured to supply the drug solution from the lumen of the drug solution container to the needle tube via the communication part of the connector and the communication passage of the puncture part. The communication part of the connector includes a first connection part connected to the second end part of the tube, and a second connection part that communicates with the lumen of the drug solution container at a position above the first connection part in a vertical direction with respect to the contact surface of the puncture part.

Further, a drug solution administering system according to the present disclosure includes a drug solution administering device having a drug solution container, a housing that holds the drug solution container, and a plunger that pushes out the drug solution in the drug solution container to the tube.

According to the administering instrument and the drug solution administering system of the present disclosure, it is possible to prevent the needle tube from coming out of a living body during administration of a drug solution.

DETAILED DESCRIPTION

Figure 1:
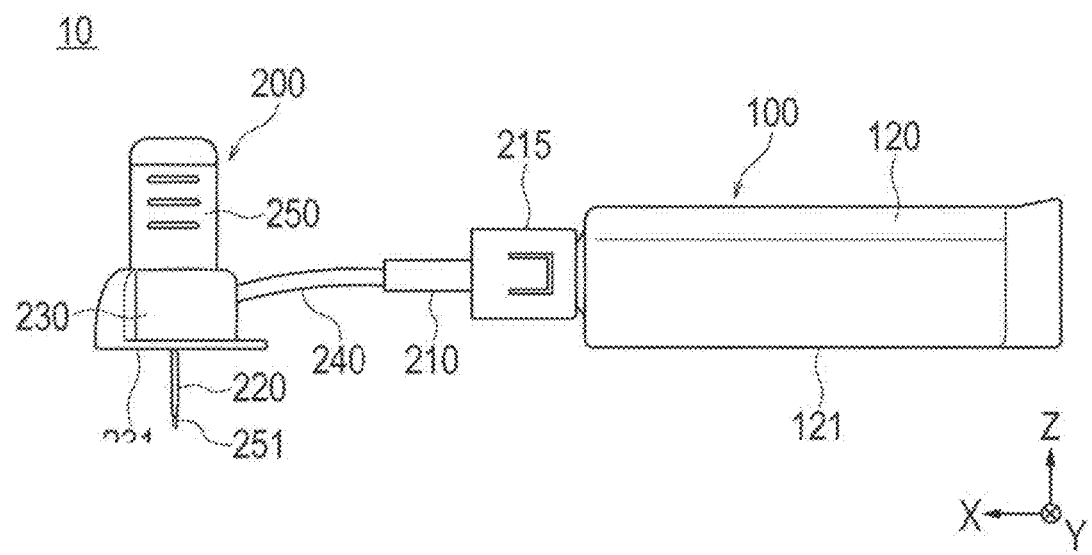
FIG. 1 is a side view of a drug solution administering system according to a first exemplary embodiment of the present disclosure.

Set forth below with reference to the accompanying drawings is a detailed description of embodiments of an administering instrument and a drug solution administering system including the administering instrument and a drug solution administering device and representing examples of the inventive administering instrument and drug solution administering system including the administering instrument, and drug solution administering device disclosed here. The following description does not limit the technical scope described in the claims and the meaning of terms used in the claims. Further, the dimensional ratios in the drawings are exaggerated for convenience of description, and may differ from the actual ratios.

First Exemplary Embodiment

Figure 2:
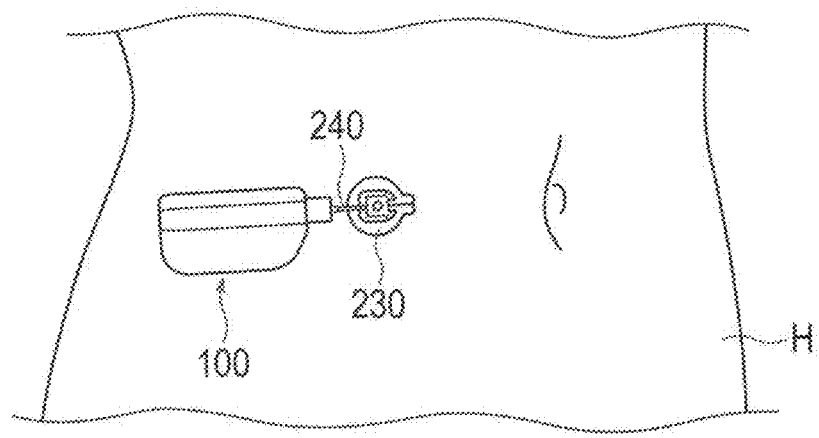
FIG. 2 is a diagram schematically illustrating an example of the use of a drug solution administering system according to the first exemplary embodiment.
Figure 3:
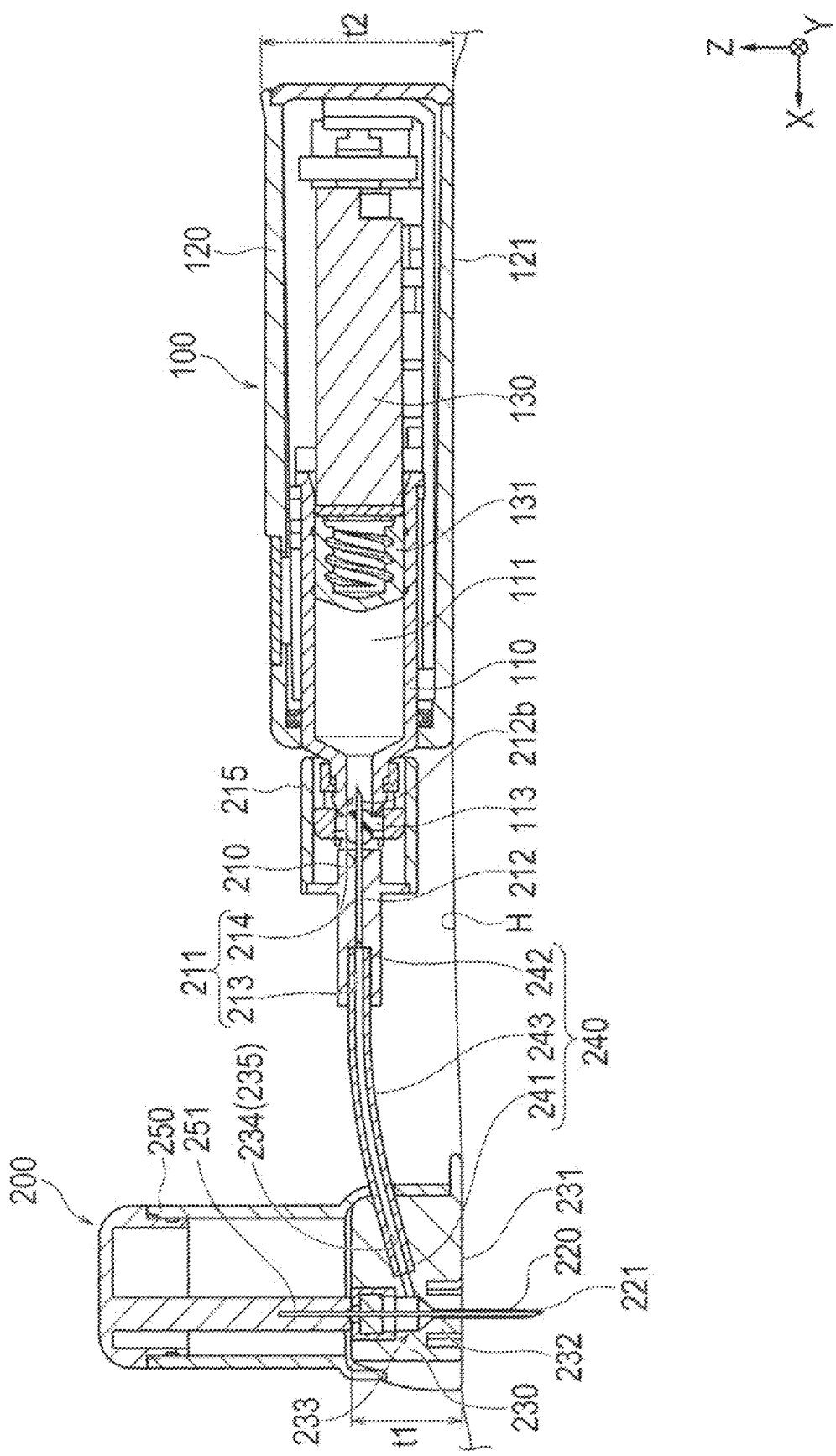
FIG. 3 is a sectional view of a drug solution administering device and an administering instrument according to the first exemplary embodiment.
Figure 4:
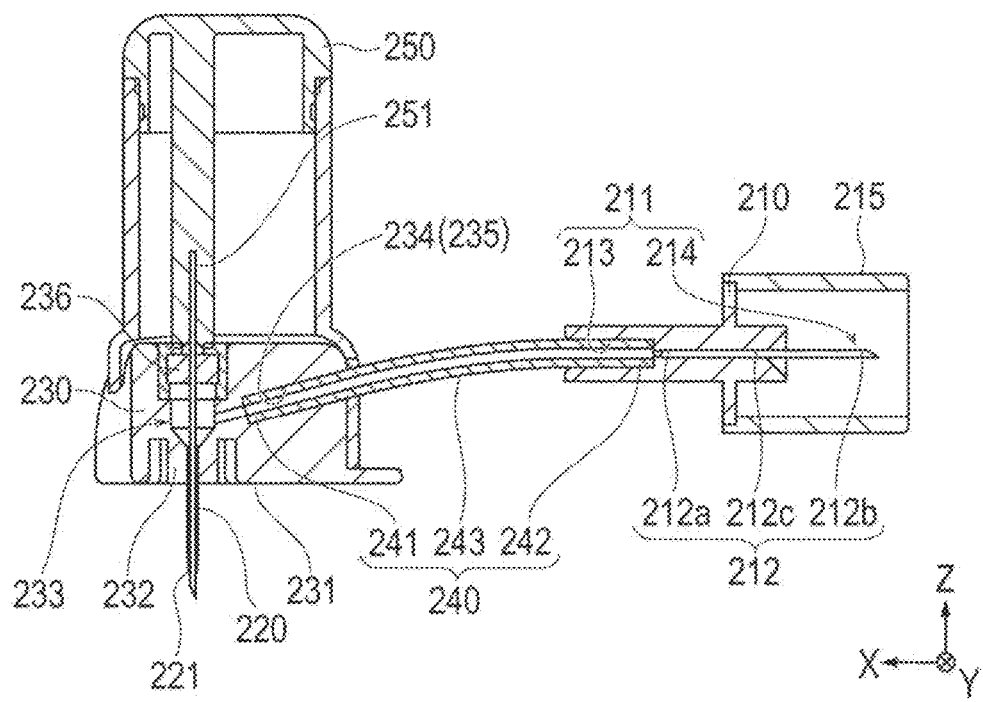
FIG. 4 is a sectional view of an administering instrument according to the first exemplary embodiment.
Figure 5:
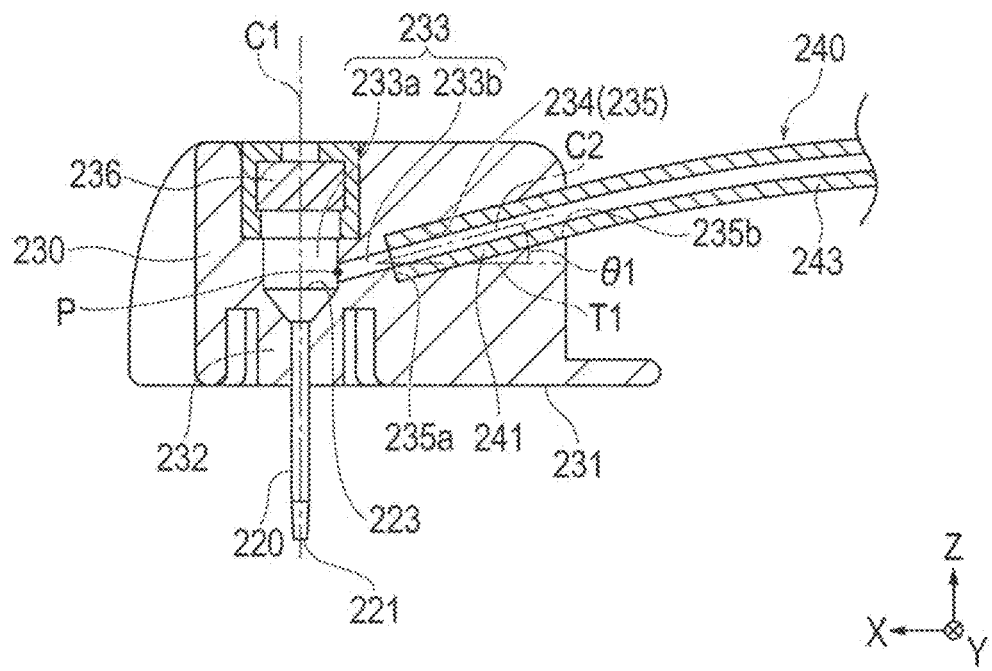
FIG. 5 is a partial enlarged sectional view of an administering instrument according to the first exemplary embodiment.

FIGS. 1 to 5 are diagrams for explaining a drug solution administering system 10, a drug solution administering device 100, and an administering instrument 200 according to the first exemplary embodiment. In the diagrams, an arrow X indicates a "longitudinal direction (extending direction of a tube 240)" of the drug solution administering device 100 and the administering instrument 200, an arrow Y indicates a "width direction (depth direction)" of the drug solution administering device 100 and the administering instrument 200, and an arrow Z indicates a "height direction (thickness direction of a puncture part 230)" of the drug solution administering device 100 and the administering instrument 200. Further, each sectional view illustrated in FIGS. 3, 4, and 5 is a longitudinal sectional view (sectional view taken along the section X-Z) of the drug solution administering device 100 and the administering instrument 200.

Drug Solution Administering System

The drug solution administering system 10 may be used to administer a drug solution to a living body. As illustrated in FIG. 1, the drug solution administering system 10 includes the drug solution administering device 100 and the administering instrument 200.

As illustrated in FIGS. 2 and 3, when the drug solution administering system 10 is used to administer a drug solution, the drug solution administering device 100 and the puncture part 230 of the administering instrument 200 are attached to a body surface H of a user. The location of the body of the user to which the drug solution administering device 100 and the puncture part 230 are attached is not limited, but may be the abdomen or thigh, for example.

The drug solution administering system 10 can continuously administer, for example, a drug solution filled in a drug solution container 110 of the drug solution administering device 100 to a living body over a relatively long period of time (for example, a few minutes to a few hours) by a pressing action of a plunger 130. The drug solution administering system 10 may intermittently administer the drug solution to the living body.

Drug Solution Administering Device

As illustrated in FIG. 3, the drug solution administering device 100 includes the drug solution container 110 in which a drug solution is filled, a housing 120 for holding the drug solution container in the housing 120, and the plunger 130 for pushing out the drug solution held in the drug solution container 110 to the tube 240 described later.

the drug solution container 110 has a cylindrical body including a lumen 111 in which the drug solution is filled. A tip of the plunger 130 is inserted into the drug solution container 110. A gasket 131 is disposed at the tip of the plunger 130. The gasket 131 can be made of, for example, a rubber material or a resin material such as an elastomer. The outer peripheral portion of the gasket 131 liquid-tightly contacts the inner peripheral surface of the drug solution container 110, which liquid-tightly seals a proximal end side of the gasket 131.

In accordance with an exemplary embodiment, the drug solution container 110, for example, is a so-called pre-filled type drug solution container. The drug solution is therefore filled, in advance, in the lumen 111 of the drug solution container 110. Examples of the drug solution include a protein preparation, a narcotic analgesic, and a diuretic.

A sealing member 113 for preventing leakage of the drug solution is provided in a tip opening (discharge port) of the drug solution container 110. The tip opening of the drug solution container 110 is disposed so as to project to the outside of the housing 120.

The plunger 130 is configured to be movable forward with respect to the drug solution container 110 toward the tip side (left side in FIG. 3) of the drug solution container 110 by an advancing mechanism. The plunger 130 moves forward with respect to the drug solution container 110 to push out the drug solution to the tube 240 from the lumen 111 of the drug solution container 110.

The housing 120 accommodates a battery for supplying power necessary for each operation of the drug solution administering device 100, a substrate to which a controller unit for controlling a motor is attached, a drive mechanism for driving the advancing mechanism, and so on.

The drug solution administering device 100 is configured as a patch type device attached to the body surface (skin) H of the user and used. The housing 120 of the drug solution administering device 100 has, on a contact surface (bottom surface) 121, a sheet-like adhesive part that can be adhered to the body surface. In the initial state before the drug solution administering device 100 is attached to the user, a peelable protective sheet is attached to an adhesive surface of the adhesive part.

Administering Instrument

As illustrated in FIGS. 1 and 2, the administering instrument 200 is configured to be connectable to the drug solution administering device 100.

As outlined with reference to FIGS. 3 to 5, the administering instrument 200 includes a connector 210, a needle tube 220 to puncture a living body, the puncture part (cannula housing) 230, the tube 240, and a puncture auxiliary tool 250 for assisting the needle tube 220 in puncturing the living body.

As illustrated in FIGS. 3 and 4, the connector 210 has a communication part 211 that can communicate with the lumen 111 of the drug solution container 110. The connector 210 is configured to be connectable to the drug solution administering device 100 via a mounting part 215 fixed to the connector 210. As illustrated in FIG. 3, the mounting part 215 is externally fitted around the tip of the drug solution container 110 projecting to the outside of the housing 120, so that the mounting part 215 can be connected to the drug solution administering device 100.

As illustrated in FIGS. 3 and 4, the communication part 211 of the connector 210 includes a first connection part 213 connected to a second end part 242 of the tube 240 and a second connection part 214 communicating with the lumen 111 of the drug solution container 110.

The communication part 211 of the connector 210 includes a connection needle tube 212 that has a first end 212a disposed close to the second end part 242 of the tube 240, a second end 212b capable of puncturing the sealing member 113 of the drug solution container 110, and an intermediate part 212c formed between the first connection part 213 and the second connection part 214.

The first end 212a of the connection needle tube 212 is fixed to the connector 210. The first end 212a of the connection needle tube 212 projects from the connector 210 toward a lumen of the mounting part 215.

The first connection part 213 of the communication part 211 is constituted by an insertion hole into which the second end part 242 of the tube 240 is inserted and fixed. The second connection part 214 of the communication part 211 is constituted by the second end 212b of the connection needle tube 212.

The tube 240 and the lumen 111 of the drug solution container 110 communicate with each other in a state (state illustrated in FIG. 3) where the connector 210 is connected to the drug solution administering device 100 through the mounting part 215 and where the second end 212b of the connection needle tube 212 penetrates the sealing member 113 of the drug solution administering device 100.

As illustrated in FIGS. 4 and 5, the puncture part 230 includes a contact surface 231 that is a lower end of the puncture part 230 and comes into contact with the body surface H of the user, a needle holding part 232 that is disposed above the contact surface 231 and holds the needle tube 220 so that a tip (lower end) 221 of the needle tube 220 projects from the contact surface 231, a communication passage 233 that communicates with a lumen of the needle tube 220, and a fixing part 234 that is disposed above the contact surface 231 and fixes a first end part 241 of the tube 240 to the puncture part 230 with the first end part 241 of the tube 240 inclined toward the contact surface 231 of the puncture part 230.

The tube 240 is configured so that a drug solution can be supplied from the lumen 111 of the drug solution container 110 to the needle tube 220 via the communication part 211 of the connector 210 and the communication passage 233 of the puncture part 230. As illustrated in FIGS. 3 and 4, the tube 240 includes the first end part 241 connected to the puncture part 230, the second end part 242 connected to the connector 210, and a tube body 243 extending from the first end part 241 to the second end part 242.

The "first end part 241" and the "second end part 242" in the present exemplary embodiment do not specify the exact positions of the tube 240, but represent a certain range of a part of the tube 240 fixed to (inserted into) the puncture part 230 and a certain range of a part of the tube 240 fixed to (inserted into) the connector 210.

The tube 240 can be formed, for example, to have a total length (length in a state where the first end part 241, the second end part 242, and the tube body 243 are linearly extended) of 10 mm to 150 mm. The first end part 241 of the tube 240 can be formed to have a length (length in a state where the portion inserted into the puncture part 230 is linearly extended) of 2 mm to 20 mm, for example. The second end part 242 of the tube 240 can be formed to have a length (length of the part inserted into the connector 210) of 2 mm to 20 mm, for example. The tube body 243 of the tube 240 can be formed to have a length (length of the part exposed from the puncture part 230 and the connector 210) of 6 mm to 146 mm, for example.

The tube 240 can be made of, for example, a hollow member made of resin having flexibility. Examples of the material of the tube 240 can include polyethylene, polypropylene, polybutadiene, polyolefin such as ethylene-propylene copolymer and ethylene-vinyl acetate copolymer, thermoplastic resin such as flexible polyvinyl chloride, various rubbers such as silicone rubber and latex rubber, and various elastomers such as polyurethane elastomer, polyamide elastomer, and polyester elastomer.

As illustrated in FIG. 4, in order to supply the drug solution to the user, the puncture auxiliary tool 250 is attached to the puncture part 230. The puncture auxiliary tool 250 holds an introducer needle (inner needle) 251. The introducer needle 251 is inserted into the communication passage 233 of the puncture part 230 and the lumen of the needle tube 220 in a state where the puncture auxiliary tool 250 is attached to the puncture part 230. In this state, a tip of the introducer needle 251 projects from the tip 221 of the needle tube 220. The user can insert the needle tube 220 into the living body by puncturing the living body with the needle tube 220 with the introducer needle 251 inserted into the needle tube 220 while, for example, preventing the needle tube 220 from being broken.

The puncture auxiliary tool 250 is detached from the puncture part 230 after the needle tube 220 punctures the living body. The introducer needle 251 is removed from the lumen of the needle tube 220 when the puncture auxiliary tool 250 is detached from the puncture part 230. As illustrated in FIG. 5, the tip 221 of the needle tube 220 is formed to be a pointed end so that the tip 221 can be inserted into the living body, and the needle tube 220 is formed, for example, to have a tapered shape toward a proximal end 223 in the vicinity of the proximal end 223 so that the drug solution flows efficiently from the communication passage 233 to the lumen of the needle tube 220.

When the introducer needle 251 is removed, in the needle tube 220, the lumen of the needle tube 220 communicates with the communication passage 233 of the puncture part 230. Further, the lumen of the needle tube 220 communicates with the lumen of the tube 240 via the communication passage 233. The administering instrument 200 administers, to the living body, the drug solution fed from the drug solution container 110 of the drug solution administering device 100 via the tube 240 with the needle tube 220 puncturing the living body. In the vicinity of the proximal end (near the upper end) of the communication passage 233, a sealing member 236 is disposed to prevent the leakage of the drug solution from the proximal end of the communication passage 233.

The introducer needle 251 can be a metal needle, for example. Further, the needle tube 220 can be, for example, a tubular member (cannula) made of resin.

The puncture auxiliary tool 250 can be prepared in a state of being attached in advance to the puncture part 230, for example, before the use of the drug solution administering system 10. In the present exemplary embodiment, the needle tube 220 may be, for example, a double needle that punctures the living body with the introducer needle 251 inserted. For example, instead of such a double needle structure, the needle tube 220 may have a structure that enables the living body to be punctured only with the needle tube 220. In the case of a structure that enables the living body to be punctured only with the needle tube 220, the needle tube 220 is preferably configured by a metal needle.

As illustrated in FIG. 5, the communication passage 233 of the puncture part 230 includes a first channel 233a extending from the proximal end 223 of the needle tube 220 along an axis C1 of the needle tube 220 and a second channel 233b that extends from a side part of the first channel 233a in a direction intersecting the axis C1 of the needle tube 220 and communicates the first channel 233a and the first end part 241 of the tube 240 with each other.

An intersection P of the first channel 233a and the second channel 233b is disposed at a position close to the proximal end 223 of the needle tube 220.

As illustrated in FIG. 5, the fixing part 234 of the puncture part 230 has an insertion hole 235 that communicates with the second channel 233b. The first end part 241 of the tube 240 is inserted into the insertion hole 235 and fitted into insertion hole 235, and thereby is fixed with respect to the puncture part 230.

In accordance with an exemplary embodiment, the tube 240 can be arranged that an axis C2 of the tube 240 at the first end part 241 is inclined, for example, by 5 degrees to 45 degrees, and preferably, by 5 degrees to 30 degrees, with respect to the contact surface 231 of the puncture part 230, for example. FIG. 5 indicates 61, which is an inclination angle (an angle at which the axis C2 is inclined) formed by the axis C2 of the tube 240 and a virtual plane T1 parallel to the contact surface 231.

As illustrated in FIG. 5, the insertion hole 235 of the puncture part 230 includes an adjacent end 235a adjacent to the second channel 233b of the communication passage 233 and an opening end 235b opposite to the adjacent end 235a (right side in FIG. 5). The opening end 235b of the insertion hole 235 is disposed above (upper side in FIG. 5) the adjacent end 235a of the insertion hole 235.

As illustrated in FIG. 5, the insertion hole 235 of the puncture part 230 is formed in a straight line from the adjacent end 235a to the vicinity of the opening end 235b. For this reason, the axis C2 of the first end part 241 of the tube 240 inserted into the insertion hole 235 extends substantially linearly (i.e., straight) from the adjacent end 235a to the vicinity of the opening end 235b.

As illustrated in FIG. 5, the projecting direction of the needle tube 220 from the contact surface 231 is substantially perpendicular to the contact surface 231. Thus, the axis C1 of the needle tube 220 intersects the contact surface 231 substantially perpendicularly.

As illustrated in FIG. 3, the puncture part 230 of the administering instrument 200 has a thickness (dimension in the horizontal direction illustrated in FIG. 3) t1 smaller than a thickness t2 of the housing 120 of the drug solution administering device 100. It should be noted that, in a state where the puncture part 230 is placed on a horizontal plane, a thickness t1 of the puncture part 230 is a dimension of a portion having the largest thickness of the puncture part 230. Similarly, in a state where the housing 120 is placed on a horizontal plane, the thickness t2 of the housing 120 is a dimension of a portion having the largest thickness of the housing 120.

In accordance with an exemplary embodiment, the puncture part 230 can be formed to have a thickness t1 of 3 mm to 30 mm, for example. Further, the housing 120 can be formed to have a thickness t2 of 10 mm to 30 mm, for example.

As with the drug solution administering device 100, the administering instrument 200 is configured as a patch type instrument adhered to the body surface H of the user and used. The puncture part 230 of the administering instrument 200 includes, on a contact surface (bottom surface) 231, a sheet-like adhesive part that can be adhered to the body surface. In the initial state before the administering instrument 200 is attached to the user, a peelable protective sheet is attached to an adhesive surface of the adhesive part.

In a case where the administering instrument 200 punctures the living body with the puncture auxiliary tool 250 attached to the puncture part 230 and the tip of the introducer needle 251 projecting from the tip 221 of the needle tube 220, the contact surface 231 of the puncture part 230 is adhered to the body surface of the user. The puncture auxiliary tool 250 is detached after the needle tube 220 punctures the living body, and the puncture part 230 remains on the body surface H of the user in a state where the needle tube 220 punctures the living body. In this state, the plunger 130 of the drug solution administering device 100 moves forward in the drug solution container 110, which allows the drug solution filled in the lumen 111 of the drug solution container 110 of the drug solution administering device 100 to be fed to the lumen of the needle tube 220 via the communication part 211 of the connector 210, the tube 240, and the communication passage 233 of the puncture part 230.

As described above, the administering instrument 200 according to the present exemplary embodiment includes the connector 210 that includes the communication part 211 capable of communicating with the lumen 111 of the drug solution container 110 and is connectable to the drug solution administering device 100, the needle tube 220 that punctures the living body, the puncture part 230 including the contact surface 231 that is provided in a lower end to contact the body surface H of the living body, the needle holding part 232 that is provided above the contact surface 231 to hold the needle tube 220 so that a tip of the needle tube 220 projects from the contact surface 231, and the communication passage 233 communicating with the lumen of the needle tube 220; and the tube 240 that includes the first end part 241 connected to the puncture part 230, the second end part 242 connected to the connector 210, and the tube body 243 communicating from the first end part 241 to the second end part 242 and is configured to supply the drug solution from the lumen 111 of the drug solution container 110 to the needle tube 220 via the communication part 211 of the connector 210 and the communication passage 233 of the puncture part 230. The puncture part 230 is disposed above the contact surface 231 and includes the fixing part 234 that fixes the first end part 241 of the tube 240 to the puncture part 230 in a state where the first end part 241 of the tube 240 is inclined toward the contact surface 231 of the puncture part 230.

In accordance with an exemplary embodiment, the administering instrument 200 may be disposed in such a manner that, for example, in a state where the puncture part 230 and the housing 120 are attached to the curved body surface H of the user and so on, the position of the contact surface 121 of the housing 120 is higher than the position of the contact surface 231 of the puncture part 230 (the distance away from the body surface H is larger in the contact surface 121 of the housing than in the contact surface 231 of the puncture part 230). In accordance with an exemplary embodiment, in a case where the puncture part 230 is formed to have a relatively thin shape in consideration of convenience at the use of the administering instrument 200 (such as avoiding the interference of the administering instrument 200 attached to the body surface H), the thickness t1 of the puncture part 230 is smaller than the thickness t2 of the housing 120; therefore, the deviation in the height direction between the contact surface 231 of the puncture part 230 and the contact surface 121 of the housing 120 may be relatively significant. When the user moves such as twisting his/her body, due to the deviation in the height direction at the time of attachment to the body surface H as described above, a force that lifts the puncture part 230 from the drug solution administering device 100 side toward the puncture part 230 acts via the first end part 241 of the tube 240 fixed to the puncture part 230. This force may remove the puncture part 230 from the body surface H and the needle tube 220 held by the puncture part 230 may come out of the living body.

In light of the foregoing issues, in the administering instrument 200 according to the present exemplary embodiment, the first end part 241 of the tube 240 may be fixed to the puncture part 230 as to be inclined toward the contact surface 231 of the puncture part 230. Therefore, even when attachment to the body surface H is performed that the position of the contact surface 121 of the housing 120 is higher than the position of the contact surface 231 of the puncture part 230, a force acting on the puncture part 230 from the drug solution administering device 100 side via the tube 240 (force that lifts the puncture part 230) can be greatly reduced. Therefore, the administering instrument 200 can suitably prevent the needle tube 220 from coming out of the living body during administration of the drug solution.

Further, in the administering instrument 200, the tube 240 may be arranged that the axis C2 of the tube 240 at the first end part 241 is inclined, for example, by 5 degrees to 45 degrees with respect to the contact surface 231 of the puncture part 230. The first end part 241 of the tube 240 is therefore fixed at a relatively gentle inclination angle with respect to the puncture part 230, which helps prevent the first end part 241 of the tube 240 from kinking. It should be noted that the inclination angle of the axis C2 of the tube 240 with respect to the contact surface 231 of the puncture part 230 can be, for example, preferably 10 degrees to 30 degrees.

Further, in the administering instrument 200, the communication passage 233 of the puncture part 230 includes the first channel 233a extending from the proximal end 223 of the needle tube 220 along the axis C1 of the needle tube 220 and the second channel 233b that extends from a side part of the first channel 233a in a direction intersecting the axis C1 of the needle tube 220 and communicates the first channel 233a and the first end part 241 of the tube 240 with each other. The intersection P of the first channel 233a and the second channel 233b is disposed at a position close to the proximal end 223 of the needle tube 220. As described above, since the intersection P of the first channel 233a and the second channel 233b is disposed at a position close to the proximal end 223 of the needle tube 220, it is possible to prevent a distance between the proximal end 223 of the needle tube 220 and the part (intersection P) where the individual channels 233a and 233b join from increasing unnecessarily. Thereby, the thickness t1 of the puncture part 230 can be reduced, leading to a reduction in the thickness of the puncture part 230.

In the administering instrument 200, the fixing part 234 of the puncture part 230 has the insertion hole 235 communicating with the second channel 233b. The fixing part 234 can therefore fix the first end part 241 of the tube 240 to the puncture part 230 more reliably, and can help prevent the first end part 241 of the tube 240 from kinking with the first end part 241 fixed to the puncture part 230.

Further, in the administering instrument 200, the insertion hole 235 of the puncture part 230 includes the adjacent end 235a adjacent to the second channel 233b of the communication passage 233 and the opening end 235b opposite to the adjacent end 235a. Then, the opening end 235b of the insertion hole 235 is disposed above the adjacent end 235a of the insertion hole 235. The insertion hole 235 can therefore fix the first end part 241 of the tube 240 more reliably in a state where the first end part 241 of the tube 240 is inclined toward the tip 221 of the needle tube 220.

Further, in the administering instrument 200, the insertion hole 235 of the puncture part 230 is formed in a straight line from the adjacent end 235a to the vicinity of the opening end 235b. Therefore, since the axis C2 of the first end part 241 of the tube 240 is straight, it is possible to reduce the pressure loss of the drug solution supplied to the communication passage 233 via the first end part 241 of the tube 240.

Further, in the administering instrument 200, the projecting direction of the needle tube 220 from the contact surface 231 is substantially perpendicular to the contact surface 231, which allows the needle tube 220 to puncture the body surface H more reliably by a simple operation of bringing the puncture part 230 closer to the body surface H. Further, since the projecting direction of the needle tube 220 from the contact surface 231 is substantially perpendicular to the contact surface 231, it is possible to reduce the pressure loss of the drug solution supplied to the living body through the needle tube 220.

Further, the drug solution administering system 10 according to the present exemplary embodiment includes the administering instrument 200 and the drug solution administering device 100 that has the drug solution container 110, the housing 120 for holding the drug solution container 110 in the housing 120, the plunger 130 for pushing out the drug solution in the drug solution container 110 to the tube 240. According to the drug solution administering system 10, it is possible to reduce a force acting on the puncture part 230 (force that lifts the puncture part 230) during administration of the drug solution and suitably prevent the needle tube 220 held in the puncture part 230 from coming out of the living body.

Further, in the drug solution administering system 10, the thickness t1 of the puncture part 230 of the administering instrument 200 is smaller than the thickness t2 of the housing 120 of the drug solution administering device 100. According to the drug solution administering system 10, it is therefore possible to reduce the thickness of the puncture part 230 and suitably prevent the occurrence of a problem that the needle tube 220 held in the puncture part 230 comes out of the living body due to the reduction in thickness of the puncture part 230.

Second Exemplary Embodiment

The description goes on to a drug solution administering system 10A, a drug solution administering device 100A, and an administering instrument 200A according to the second exemplary embodiment. The same configurations as those in the first embodiment are denoted by the same reference numerals and description of the same reference numerals is omitted. In addition, configurations not particularly mentioned in the second exemplary embodiment can be configured in substantially the same manner as described above in the first embodiment.

Figure 6:
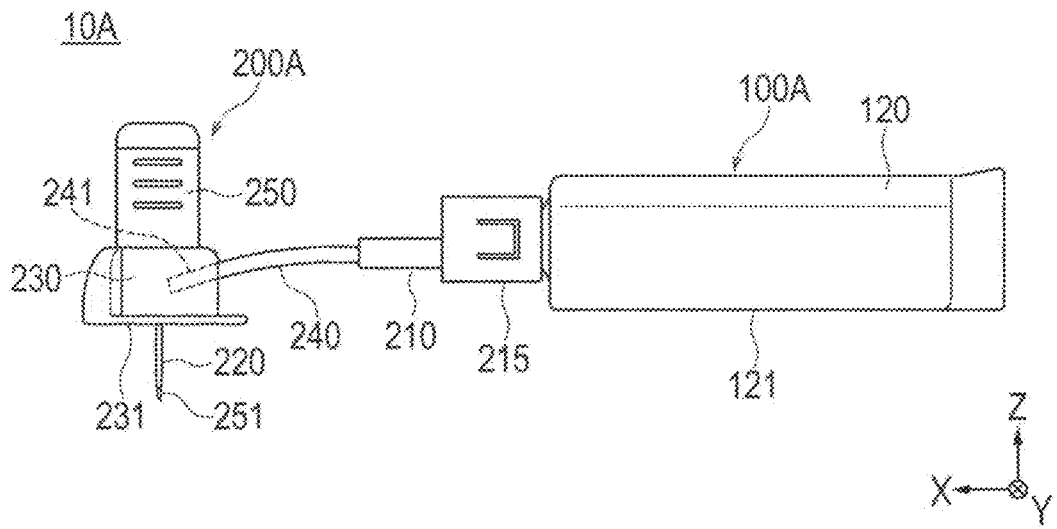
FIG. 6 is a side view of a drug solution administering system according to a second exemplary embodiment of the present disclosure.
Figure 7:
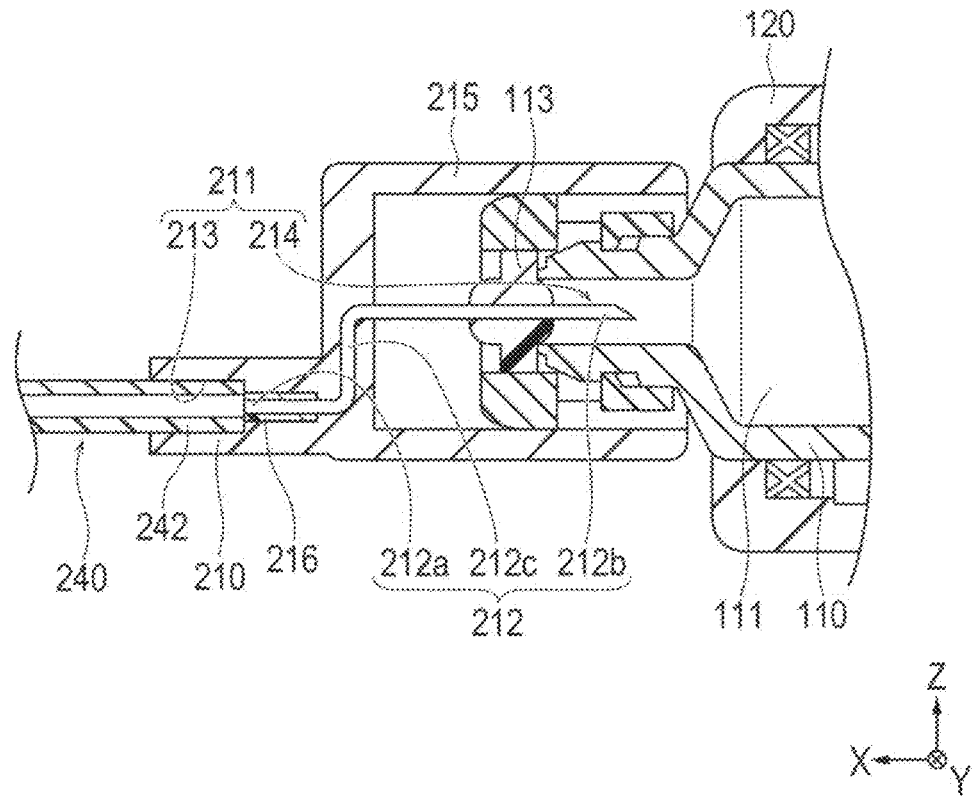
FIG. 7 is a partial enlarged sectional view of a drug solution administering device and an administering instrument according to the second exemplary embodiment.

FIGS. 6 and 7 are diagrams illustrating the drug solution administering system 10A, the drug solution administering device 100A, and the administering instrument 200A according to the second exemplary embodiment.

The administering instrument 200 according to the first exemplary embodiment described above is configured that the first end part 241 of the tube 240 is inclined toward the contact surface 231 and fixed at the fixing part 234 of the puncture part 230, and thereby a force acting on the puncture part 230 (force that lifts the puncture part 230) during administration of the drug solution can be reduced. In accordance with an exemplary embodiment, as illustrated in FIGS. 6 and 7, the administering instrument 200A according to the second exemplary embodiment includes, on the side of the communication part 211 of the connector 210, a configuration for reducing the force acting on the puncture part 230. It should be noted that the first end part 241 of the tube 240 is fixed to the fixing part 234 (insertion hole 235) of the puncture part 230 as with the first exemplary embodiment (see FIG. 5).

As illustrated in FIG. 7, the connector 210 has the communication part 211 that can communicate with the lumen 111 of the drug solution container 110.

The communication part 211 of the connector 210 has the first connection part 213 connected to the second end part 242 of the tube 240 and the second connection part 214 communicating with the lumen 111 of the drug solution container 110 above the first connection part 213 in the vertical direction (the vertical direction in FIG. 7) with respect to the contact surface 231 of the puncture part 230.

The communication part 211 of the connector 210 includes the connection needle tube 212 that has the first end 212a disposed close to the second end part 242 of the tube 240, the second end 212b that constitutes the second connection part 214 and can puncture the sealing member 113 of the drug solution container 110, and the intermediate part 212c that is formed between the first connection part 213 and the second connection part 214 and extends so that at least a portion of the intermediate part 212c may be bent in the vertical direction.

As illustrated in FIG. 7, the connector 210 and the mounting part 215 are integrally formed. The connection needle tube 212 is insert molded in the connector 210 and the mounting part 215. The connection needle tube 212 may be molded as a resin molding integrated with the connector 210 and the mounting part 215. In the vicinity of the first end 212a of the connection needle tube 212, a seal member 216 is disposed which helps prevent leakage of the drug solution between the connection needle tube 212 and the tube 240.

The intermediate part 212c of the connection needle tube 212 is formed to be bent so as to be substantially perpendicularly from the first end 212a side to the second end 212b side. However, the specific shape of the intermediate part 212c is not limited. The intermediate part 212c may be bent or curved a plurality of times, for example, from the first end 212a side to the second end 212b side. Further, the bending angle, the curvature of curve, and so on are not limited.

The administering instrument 200A according to the exemplary embodiment described above includes the connector 210 that includes the communication part 211 capable of communicating with the lumen 111 of the drug solution container 110 and is connectable to the drug solution administering device 100A, the needle tube 220 that punctures the living body, the puncture part 230 including the contact surface 231 that is provided in a lower end to contact the body surface H of the living body, the needle holding part 232 that is provided above the contact surface 231 to hold the needle tube 220 so that a tip of the needle tube 220 projects from the contact surface 231, and the communication passage 233 communicating with the lumen of the needle tube 220; and the tube 240 that includes the first end part 241 connected to the puncture part 230, the second end part 242 connected to the connector 210, and the tube body 243 communicating from the first end part 241 to the second end part 242 and is configured to supply the drug solution from the lumen 111 of the drug solution container 110 to the needle tube 220 via the communication part 211 of the connector 210 and the communication passage 233 of the puncture part 230. The communication part 211 of the connector 210 includes the first connection part 213 connected to the second end part 242 of the tube 240, and the second connection part 214 that communicates with the lumen 111 of the drug solution container 110 at a position above the first connection part 213 in a vertical direction with respect to the contact surface 231 of the puncture part 230.

In the administering instrument 200A according to the present exemplary embodiment, the second connection part 214 of the communication part 211 of the connector 210 communicates with the lumen 111 of the drug solution container 110 at a position above the first connection part 213. Thus, even in a case where the puncture part 230 and the housing 120 are disposed so that the position of the contact surface 121 of the housing 120 is higher than the position of the contact surface 231 of the puncture part 230 in a state where the puncture part 230 and the housing 120 are attached to the body surface H, a force acting on the puncture part 230 from the drug solution administering device 100A side via the tube 240 (force that lifts the puncture part 230) may be greatly reduced. Therefore, the administering instrument 200A can suitably prevent the needle tube 220 from coming out of the living body during administration of the drug solution, as with the administering instrument 200 of the first exemplary embodiment.

Further, in the administering instrument 200A, the communication part 211 of the connector 210 includes the connection needle tube 212 that has the first end 212a disposed close to the second end part 242 of the tube 240, and the second end 212b that constitutes the second connection part 214 and is capable of puncturing the sealing member 113 of the drug solution container 110, and the intermediate part 212c that is formed between the first connection part 213 and the second connection part 214 and extends in such a manner that at least a part of the intermediate part 212c is bent in the vertical direction. For this reason, a step in the height direction can be provided between the first connection part 213 and the second connection part 214 by forming the connection needle tube 212 in a predetermined shape. Therefore, a structure for preventing the needle tube 220 from coming off can be added to the administering instrument 200A by a simple manufacturing process for processing the shape of the connection needle tube 212.

The communication part 211 may be configured, for example, by the connector 210 and the mounting part 215 instead of the connection needle tube. In this case, a lumen (channel) in which a step (i.e., a difference of height) in the vertical direction between the connector 210 and the mounting part 215 is formed, and a projection capable of puncturing the sealing member 113 is provided in an end on the sealing member 113 side of the mounting part 215. The connector 210 and the mounting part 215 are formed as described above, which can demonstrate the same effect as that of the administering instrument 200A described in the second exemplary embodiment.

The administering instrument and the drug solution administering system according to the embodiments of the present disclosure are described above. The present disclosure is not limited only to the configurations described above, and can be modified suitably on the basis of the description of claims.

For example, it is only required that the administering instrument has at least one of the configurations of the fixing part described in the first exemplary embodiment and the communication part described in the second exemplary embodiment to help prevent the needle tube from coming off during administration of the drug solution.

In addition, the material, shape, size, and arrangement of the members constituting the administering instrument and the drug solution administering system, and the connecting/coupling structures of the members of the administering instrument and the drug solution administering system are not particularly limited as long as the effects of the present disclosure are exhibited, and can be changed and replaced as desired. Moreover, it is also possible to appropriately add any constituent members or the like, which are not particularly described in the specification, to the administering instrument and the drug solution administering system.

The detailed description above describes embodiments of an administering instrument and a drug solution administering system including the administering instrument and a drug solution administering device. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. An administering instrument connectable to a drug solution administering device including a drug solution container in which a drug solution is filled, the administering instrument comprising:
 a connector that includes a communication part configured to communicate with a lumen of the drug solution container and is connectable to the drug solution administering device;
 a needle tube configured to puncture a living body;
 a puncture part including a contact surface that is provided in a lower end and configured to contact a body surface of the living body, a needle holding part that is provided above the contact surface to hold the needle tube so that a tip of the needle tube projects from the contact surface, and a communication passage communicating with a lumen of the needle tube;
 a tube that includes a first end part connected to the puncture part, a second end part connected to the connector, and a tube body communicating from the first end part to the second end part and is configured to supply the drug solution from the lumen of the drug solution container to the needle tube via the communication part of the connector and the communication passage of the puncture part;
 wherein the puncture part is disposed above the contact surface and includes a fixing part that fixes the first end part of the tube to the puncture part in a state where the first end part of the tube is inclined toward the contact surface of the puncture part;
 the communication part of the connector including a first connection part connected to the second end part of the tube, and a second connection part that communicates with the lumen of the drug solution container at a position above the first connection part in a vertical direction with respect to the contact surface of the puncture part;
 the communication part of the connector including a connection needle tube that has a first end disposed close to the second end part of the tube, and a second end that constitutes the second connection part and is capable of puncturing a sealing member of the drug solution container, and an intermediate part that is formed between the first connection part and the second connection part and extends in such a manner that at least a part of the intermediate part is bent in the vertical direction; and wherein the intermediate part of the connection needle tube is curved a plurality of times from the first end of the connection needle tube to the second end of the connection needle tube.

2. The administering instrument according to claim 1, wherein an axis of the tube at the first end part is inclined by 5 degrees to 45 degrees with respect to the contact surface of the puncture part.

3. The administering instrument according to claim 1, wherein the communication passage of the puncture part includes a first channel that extends from a proximal end of the needle tube along an axis of the needle tube and a second channel that extends from a side part of the first channel in a direction intersecting the axis of the needle tube and communicates the first channel and the first end part of the tube with each other, and an intersection of the first channel and the second channel is provided at a position close to the proximal end of the needle tube.

4. The administering instrument according to claim 3, wherein the fixing part communicates with the second channel and includes an insertion hole into which the first end part of the tube is inserted.

5. The administering instrument according to claim 4, wherein the insertion hole includes an adjacent end adjacent to the second channel and an opening end opposite to the adjacent end; and the opening end is disposed above the adjacent end.

6. The administering instrument according to claim 5, wherein the insertion hole is formed in a straight line from the adjacent end to the opening end.

7. The administering instrument according to claim 1, wherein a projecting direction of the needle tube from the contact surface is substantially perpendicular to the contact surface.

8. The administering instrument according to claim 1, wherein the intermediate part of the connection needle tube is substantially perpendicular to a side of the first end of the connection needle tube and to a side of the second end of the connection needle tube.

9. The administering instrument according to claim 1, further comprising:

a seal member disposed on the first end of the connection needle tube, the seal member configured to prevent leakage of the drug solution between the connection needle tube and the tube.

10. The administering instrument according to claim 1, wherein the connector includes a mounting part fixed to the connector, the mounting part configured to be externally fitted around a tip of the drug solution container projecting to an outside of a housing of the drug solution container.

11. A drug solution administering system comprising:

an administering instrument connectable to a drug solution administering device, the drug solution administering device including a drug solution container in which a drug solution is filled, the administering instrument comprising:

a connector that includes a communication part configured to communicate with a lumen of the drug solution container and is connectable to the drug solution administering device;

a needle tube configured to puncture a living body;

a puncture part including a contact surface that is provided in a lower end and configured to contact a body surface of the living body, a needle holding part that is provided above the contact surface to hold the needle tube so that a tip of the needle tube projects from the contact surface, and a communication passage communicating with a lumen of the needle tube;

a tube that includes a first end part connected to the puncture part, a second end part connected to the connector, and a tube body communicating from the first end part to the second end part and is configured to supply the drug solution from the lumen of the drug solution container to the needle tube via the communication part of the connector and the communication passage of the puncture part;

wherein the puncture part is disposed above the contact surface and includes a fixing part that fixes the first end part of the tube to the puncture part in a state where the first end part of the tube is inclined toward the contact surface of the puncture part;

the communication part of the connector including a first connection part connected to the second end part of the tube, and a second connection part that communicates with the lumen of the drug solution container at a position above the first connection part in a vertical direction with respect to the contact surface of the puncture part; and wherein the communication part of the connector includes a connection needle tube that has a first end disposed close to the second end part of the tube, and a second end that constitutes the second connection part and is capable of puncturing a sealing member of the drug solution container, and an intermediate part that is formed between the first connection part and the second connection part and extends in such a manner that at least a part of the intermediate part is bent in the vertical direction, and wherein the intermediate part of the connection needle tube is curved a plurality of times from the first end of the connection needle tube to the second end of the connection needle tube; and a housing that holds the drug solution container, and a plunger configured to push out the drug solution in the drug solution container to the tube.

12. The drug solution administering system according to claim 11, wherein the puncture part of the administering instrument has a thickness smaller than a thickness of the housing of the drug solution administering device.

13. The drug solution administering system according to claim 11, wherein an axis of the tube at the first end part is inclined by 5 degrees to 45 degrees with respect to the contact surface of the puncture part.

14. The drug solution administering system according to claim 11, wherein the communication passage of the puncture part includes a first channel that extends from a proximal end of the needle tube along an axis of the needle tube and a second channel that extends from a side part of the first channel in a direction intersecting the axis of the needle tube and communicates the first channel and the first end part of the tube with each other, and an intersection of the first channel and the second channel is provided at a position close to the proximal end of the needle tube.

15. The drug solution administering system according to claim 14, wherein the fixing part communicates with the second channel and includes an insertion hole into which the first end part of the tube is inserted.

16. The drug solution administering system according to claim 15, wherein
the insertion hole includes an adjacent end adjacent to the second channel and an opening end opposite to the adjacent end; and
the opening end is disposed above the adjacent end.

17. The drug solution administering system according to claim 16, wherein the insertion hole is formed in a straight line from the adjacent end to the opening end.

18. The drug solution administering system according to claim 11, wherein a projecting direction of the needle tube from the contact surface is substantially perpendicular to the contact surface.

19. An administering instrument connectable to a drug solution administering device including a drug solution container in which a drug solution is filled, the administering instrument comprising:
a connector that includes a communication part configured to communicate with a lumen of the drug solution container and is connectable to the drug solution administering device;
a needle tube configured to puncture a living body;
a puncture part including a contact surface that is provided in a lower end and configured to contact a body surface of the living body, a needle holding part that is provided above the contact surface to hold the needle tube so that a tip of the needle tube projects from the contact surface; and a communication passage communicating with a lumen of the needle tube;
a tube that includes a first end part connected to the puncture part, a second end part connected to the connector, and a tube body communicating from the first end part to the second end part and is configured to supply the drug solution from the lumen of the drug solution container to the needle tube via the communication part of the connector and the communication passage of the puncture part;

the communication part of the connector including a first connection part connected to the second end part of the tube, and a second connection part that communicates with the lumen of the drug solution container at a position above the first connection part in a vertical direction with respect to the contact surface of the puncture part; and wherein the communication part of the connector includes a connection needle tube that has a first end disposed close to the second end part of the tube, and a second end that constitutes the second connection part and is capable of puncturing a sealing member of the drug solution container, and an intermediate part that is formed between the first connection part and the second connection part and extends in such a manner that at least a part of the intermediate part is bent in the vertical direction, and wherein the intermediate part of the connection needle tube is curved a plurality of times from the first end of the connection needle tube to the second end of the connection needle tube.

* * * * *